United States Patent [19]

Fleche et al.

[11] Patent Number: 5,872,247
[45] Date of Patent: Feb. 16, 1999

[54] DECARBOXYLATION PROCESS FOR 2-KETOALDONIC ACIDS

[76] Inventors: Guy Fleche, 15 Rue Gambetta, 59190 Hazebrouck; Pierrick Duflot, 773 Rue de la neuve voie, 62136 Lacouture, both of France

[21] Appl. No.: 864,780

[22] Filed: May 29, 1997

[30] Foreign Application Priority Data

Jun. 3, 1996 [FR] France .................................. 96 06808

[51] Int. Cl.$^6$ .............................. C07H 1/00; C07H 7/027
[52] U.S. Cl. ......................... 536/124; 536/1.11; 536/125
[58] Field of Search ................................... 536/1.11, 124, 536/125

[56] References Cited

U.S. PATENT DOCUMENTS 5,096,820  3/1992  Leleu et al. .............................. 435/158

FOREIGN PATENT DOCUMENTS 0 716 067  6/1996  European Pat. Off. .
811632  10/1997  European Pat. Off. .

WO 93/19030  9/1993  WIPO .

OTHER PUBLICATIONS

Agr. Biol. Chem., vol. 27, No. 3, 1963, pp. 180–184.
Collins and Ferrier. *Monosaccarides: Their Chemistry and their Roles in Natural Products*, pp. 135–138, (1995). (John Wiley & Sons).
Pigman and Goepp. *Chemistry of the Carbohydrates*, pp. 336–339, (1948). (Academic Press, Inc.).
John Green, Chapter VI "Acids and Oxidation Products" from *The Carbohydrates*, ed. by Ward Pigman, pp. 325–328, (1957). (Academic Press).

*Primary Examiner*—John Kight
*Assistant Examiner*—Howard C. Lee
*Attorney, Agent, or Firm*—Henderson & Sturm

[57] ABSTRACT

Catalytic decarboxylation process for 2-ketoaldonic acids by nickel ions characterized in that an aqueous solution of a 2-ketoaldonic acid is put in contact with a resin carrying vinylpyridine groups.

The process allows in particular ribulose, xylulose and erythrulose to be easily obtained.

12 Claims, No Drawings

DECARBOXYLATION PROCESS FOR 2-KETOALDONIC ACIDS

The present invention concerns a specific decarboxylation process for 2-ketoaldonic acids.

More precisely, the present invention concerns a decarboxylation process for 2-ketoaldonic acids catalyzed by nickel ions, and taking place in aqueous phase.

The process according to the invention allows the ketose of the corresponding functionality immediately lower than this aldonic acid to be obtained with an excellent yield.

Thus the process according to the invention allows for example, the following to be obtained:

D-ribulose starting from 2-keto-D-gluconic acid,

D-xylulose starting from 2-keto-D-galactonic acid,

D-erythrulose starting from 2-keto-D-arabinonic acid.

These ketoses, which are rare in nature, are of great interest as they are, but above all they would be highly important synthesis intermediates if they could be produced in large quantities and at low cost. In fact, simple complementary stages of hydrogenation and/or isomerization of these ketoses allow xylitol, D-arabitol, D-ribitol, D-threitol or erythritol to be easily obtained, all the latter being polyols which can be used in multiple applications and in particular as non-cariogenic and low-calory substitutes for sucrose.

A decarboxylation process for certain 2-ketoaldonic acids exists which produces with excellent yields the ketoses of the corresponding functionality immediately lower than these acids.

This process, described by MATSUI et al. in Agr. Biol. Chem., Vol. 27, No. 3. p. 180 to 184, 1963, consists of subjecting certain 2-ketoaldonic acids dissolved in warm anhydrous pyridine to the decarboxylating catalytic action of $Ni^-$ ions.

In this way, the authors have shown that 2-keto-D-gluconic acid produced D-ribulose and a little of its isomer D-arabinose and that 2-keto-L-gluconic acid produced L-xylulose accompanied by lesser quantities of its isomer, L-xylose.

It is probable that in this process, the weak basic character of pyridine is responsible for the appearance of arabinose and xylose via the intermediary of an alkaline isomerization of the ribulose and xylulose formed.

Such a process, which is efficient and uses 2-ketoaldonic acids which are easily obtained from corresponding aldoses, which are plentiful and inexpensive, has never however found a place in industry, in particular the food industry.

In fact, it uses pyridine, an extremely toxic and inflammable solvent, which moreover, it is acknowledged should be used in the anhydrous state and at close to its boiling point.

In addition, the appearance via this process of isomerization products of ketoses can in certain cases prove to be a nuisance.

Therefore, a need exists to perfect an effective decarboxylation process for 2-ketoaldonic acids which does not have redhibitory drawbacks of the prior art and which is able to produce the ketoses of the corresponding functionality immediately lower than these acids with excellent yields and in a state of high purity.

And the Applicant Company has found that when an aqueous solution of a 2-ketoaldonic acid and nickel salts is put in contact with a resin carrying vinylpyridine groups the ketose of the corresponding functionality immediately lower than this acid is obtained with an excellent yield and in a state of high purity.

According to the invention, the catalytic decarboxylation process for 2-ketoaldonic acids by nickel ions is therefore characterized in that an aqueous solution of a 2-ketoaldonic acid is put in contact with a resin carrying vinylpyridine groups.

The first advantage of such a process relative to the process of the prior art is obvious both from a toxicity aspect and from a safety aspect because warm pyrdine is not used.

A second advantage of the process according to the invention resides in the fact that it is extremely easy to implement as the resin can be separated from the reaction aqueous phase by simple filtration and without the specific confinement and elimination precautions demanded by the use of an organic solvent as dangerous as pyridine.

A third advantage of the process according to the invention is that the ketose is obtained without parasitic isomerization and with a quasi-stoichiometric yield.

Preferably, the process according to the invention is implemented at a temperature comprised between 40° C. and 100° C. Lower temperatures lead to reaction times which are too long and higher temperatures, besides the fact that they would require the use of pressure-resistant reaction vessels, would lead either to a progressive degradation of the resin or to a degradation of the reaction products. Temperatures between 70° C. and 90° C. are particularly preferred for the process according to the invention.

More preferably, the process according to the invention is implemented with aqueous solutions of 2-ketoaldonic acids the concentration of which is higher than 50 g/liter, for obvious reasons of economizing on water evaporation and of reducing the size of the decarboxylation reaction vessels.

Constraints on higher concentrations are above all imposed by the solubility or viscosity problems of the reaction media and are therefore dependent on the nature of the aldonic acid subjected to decarboxylation.

However, in a general manner, aqueous solutions of aldonic acids with a concentration higher than 500 g/l will not be used.

In the process according to the invention the decarboxylation catalyst is constituted by nickel ions which can be provided in the form of any divalent nickel salt.

For example nickel acetate, chloride or nitrate are perfectly suitable.

In the process according to the invention nickel ions will advantageously be used in the form of their aqueous solution of nickel salts originating, for example, from the regeneration of cationic exchangers situated downstream from the decarboxylation stage, in which solution the 2-ketoaldonic acid which one wishes to decarboxylate will be able to be dissolved or diluted.

Concentrations, expressed in nickel, of 4 to 5% relative to the 2-ketoaldonic acid used give good results in the process according to the invention, both as regards the yield and the purity of the ketoses obtained.

The resin carrying the vinylpyridine groups used in the process according to the invention can be of a polyvinylpyridine nature or can also have a styrene-divinylbenzene skeleton.

Such resins are commercially available, for example, under the designation PVP 901 from the IONAC company or are known under the reference No. 100029 from the PUROLITE INTERNATIONAL company.

Concentrations of 50 milliliters of resin per liter of 2-ketoaldonic acid solution used give good results in the process according to the invention when this is implemented in a discontinuous manner.

In such a use, the duration of the decarboxylation reaction is of the order of one hour.

Of course, the process can be carried out in a continuous manner by percolating the 2-ketoaldonic acid solutions through a resin bed.

In this case, it is preferable to work with an ascending movement of the 2-ketoaldonic acid solutions through the resin, and in this way encourage the release of carbon dioxide which is produced during the decarboxylation of the ketoaldonic acid.

This way of working having thus been explained, simple routine operations will allow a man skilled in the art to determine the flow rates and temperatures which produce the best results in terms of productivity and selectivity of the decarboxylation reaction.

In a general manner, whether the process is carried out in a continuous or discontinuous fashion, it is preferable to carry out the decarboxylation of the 2-ketoaldonic acid until at least 75%, in a preferred manner until at least 85% and in a yet more preferred manner until at least 90% of the 2-ketoaldonic acid is decarboxylated in order to produce the ketose of the corresponding functionality immediately lower than this acid.

When the process according to the invention is implemented in a discontinuous manner, the ketose solution thus obtained is simply filtered in order to remove the resin. This resin which has been filtered out in this way can then be reused, without requiring washing, in a subsequent decarboxylation operation and can therefore be reused a large number of times without noting a loss of activity of this resin.

However, such a filtration operation is not necessary when the decarboxylation of 2-ketoaldonic acids is carried out in a continuous fashion.

After this decarboxylation operation the syrups of ketoses obtained are demineralized for example by electrodialysis or by demineralization on cationic and anionic ion exchangers regenerated in the form of hydrogen and in the form of hydroxyl respectively.

The electrodialysates or the regeneration effluents of cationic exchangers, which are rich in nickel salts, having served as the catalyst are advantageously recovered in order to dissolve again therein the 2-ketoaldonic acids which one wishes to subject to decarboxylation.

Thus the process according to the present invention allows ketoses to be obtained with excellent yields and purities having one carbon atom less than the 2-ketoaldonic acid from which they are derived and to do this without using toxic and dangerous solvents.

The process according to the present invention which allows amongst others, the obtaining of xylulose from 2-ketogalactonic acid is particularly efficient in a more specific process for obtaining xylitol from lactose.

Such a more particular process consists of hydrolyzing lactose into glucose and galactose, of oxidizing the galactose by chemical or microbial route into 2-ketogalactonic acid, of decarboxylating this acid into xylulose by the process according to the invention, then of hydrogenating this xylulose into xylitol, either as it is, or in a preferred fashion after enzymatic isomerization of this xylulose into xylose as described for example in the U.S. Pat. No. 5,096,820, of which the Applicant is an assignee.

The process according to the present invention also allows erythrulose to be obtained from 2-ketoarabinonic acid. The erythrulose thus obtained can then be converted by hydrogenation in order to obtain erythritol in an advantageous fashion.

With the process according to the invention it is also possible to obtain ribulose from 2-ketogluconic acid. The ribulose thus obtained can then be converted by hydrogenation to ribitol.

The invention will be better understood by means of the examples which follow and which have the sole purpose of better illustrating the invention without intending to reduce the implementations which are described in it or to limit it to only the 2-ketoaldonic acids used.

EXAMPLE 1

1 liter of a solution of 2-keto-D-gluconic acid is introduced into a thermostatically-controlled and agitated tank with a total volume of 1.5 liter.

This tank is heated to a temperature of 80° C. then 17 grams of hexahydrated nickel nitrate and 50 ml of PUROLITE resin No. 100029 are added to it.

This resin is an anionic resin having the vinylpyridine functional group. It has a capacity of 1.98 equivalent per liter in the form of the free base, a porosity of 0.66 ml/gram, has an average pore diameter of 678 Angstroms and a specific surface area of 51.4 $m^2$ per gram.

It is presented in the form of beads 86.8% of which have a diameter comprised between 425 and 1000 microns.

The reaction is left to develop for one hour then the reaction medium is recovered by simple filtration of the resin.

This resin is recovered and without washing it, it is recycled in a second strictly identical operation then again in a third operation.

At the end of these three trials the final reaction medium is analyzed. This only contains D-ribulose.

The results obtained are recorded in the following table in which the concentrations of 2-keto-D-gluconic acid and D-ribulose are expressed in moles per liter of filtered reaction medium.

The ribulose conversion yield is also molar.

|  | Trial 1 | Trial 2 | Trial 3 |
|---|---|---|---|
| Initial state |  |  |  |
| 2-keto-D-gluconic acid | 0.386 | 0.386 | 0.386 |
| Final state |  |  |  |
| 2-keto-D-gluconic acid | 0 | 0 | 0 |
| D-ribulose | 0.13 | 0.29 | 0.34 |
| % conversion | 100 | 100 | 100 |
| Yield | 34.2 | 76.3 | 89.5 |

This table shows that the conversion of 2-keto-D-gluconic acid into D-ribulose is total in each trial and that the yield of the reaction increases from one trial to the other.

This progressive increase in yield is due to the installation, which is also progressive, of a permanent regime where an equilibrium exists between the concentration of the external medium and the concentration of the adsorbed phase in the resin beads.

In fact, it was noted that the succession of several other trials rapidly brought the yield to a value close to 100%.

A final washing of the resin allows it to desorb the ribulose which it has adsorbed and in this way a yield close to 100% for the decarboxylation of 2-keto-D-gluconic acid into D-ribulose is obtained for the totality of the trials.

Catalytic hydrogenation of this ribulose produces an equimolecular mixture of D-ribitol and D-arabitol.

EXAMPLE 2

400 g of water in which 100 g (0.515 mole) of 2-ketogalactonic acid and 8 g (0.0275 mole) of hexahydrated nickel nitrate are introduced into a thermostatically-controlled and agitated tank.

Then 625 ml of Purolite resin No. 100029 as used in Example 1 is added.

The reaction medium is heated to 80° C. for 40 minutes under agitation.

After cooling down, the reaction medium is recovered by filtering the resin out. The resin is washed once with water. The washing water is mixed with the reaction medium. The reaction medium is analyzed. This only contains xylulose.

The conversion rate of 2-ketogalactonic acid is therefore 100%. The molar yield of xylulose is 82.5%.

EXAMPLE 3

400 g of water in which 100 g (0.609 mole) of 2-ketoarabinonic acid and 9.4 g (0.032 mole) of hexahydrated nickel nitrate are introduced into a thermostatically-controlled and agitated tank. Then 740 ml of Purolite resin No. 100029 as used in Example 1 is added.

The reaction medium is heated to 80° C. for 60 minutes under agitation.

After cooling down, the reaction medium is recovered by filtering the resin out. The resin is washed once with water. The washing water is mixed with the reaction medium. The reaction medium is analyzed. This only contains erythrulose.

The conversion rate of 2-ketoarabinonic acid is therefore 100%. The molar yield of erythrulose is 40%.

EXAMPLE 4

Example 2 is started again however the reaction medium is heated to 80° C. for 60 minutes instead of 40 minutes.

Analysis of the reaction medium shows that the conversion rate of 2-ketogluconic acid is 100%. The molar yield of ribulose is 95%. The resin can be reused at least 10 times without any reduction in its activity and its selectivity.

EXAMPLE 5

A solution containing 100 g (0.515 mole) of 2-ketogluconic acid and 8 g (0.0275 mole) of hexahydrated nickel nitrate in 400 g of water is passed in a loop through a thermostatically-controlled column containing 125 ml of Purolite resin No. 100029 as used in Example 1 at 80° C.

The feed is carried out from bottom to top in order to facilitate elimination of the carbon dioxide. The speed of passage through the column is 1V/V/h. The recirculation is stopped when the conversion of 2-ketogluconic acid is complete. The total duration of the reaction is 5 hours and the molar yield of ribulose is 70%.

We claim:

1. Catalytic decarboxylation process for 2-ketoaldonic acids by nickel ions wherein an aqueous solution of a 2-ketoaldonic acid is put in contact with a resin carrying vinylpyridine groups.

2. Catalytic decarboxylation process for 2-ketoaldonic acids by nickel ions according to claim 1, wherein the decarboxylation is carried out at a temperature from 40° to 100° C.

3. Catalytic decarboxylation process for 2-ketoaldonic acids by nickel ions according to claim 1, wherein the aqueous solution of aldonic acid is at a concentration comprised between 50 and 500 g/l.

4. Catalytic decarboxylation process for 2-ketoaldonic acids by nickel ions according to claim 1, wherein the solutions of ketoses obtained are demineralized through cationic and anionic ion exchangers regenerated in the form of hydrogen and in the form of hydroxyl respectively.

5. Catalytic decarboxylation process for 2-ketoaldonic acids by nickel ions according to claim 4, wherein the nickel ions are produced by regeneration from cationic ion exchangers.

6. Catalytic decarboxylation process for a 2-ketoaldonic acid into xylulose according to claim 1, wherein the 2-ketoaldonic acid is 2-ketogalactonic acid.

7. Production process for xylitol by hydrogenation of xylulose wherein the xylulose is obtained by the process according to claim 6.

8. Catalytic decarboxylation process for a 2-ketoaldonic acid into ribulose according to claim 1, wherein the 2-ketoaldonic acid is 2-ketogluconic acid.

9. Production process for ribitol by hydrogenation of ribulose wherein the ribulose is obtained by the process according to claim 8.

10. Catalytic decarboxylation process for a 2-ketoaldonic acid into erythrulose according to claim 1, wherein the 2-ketoaldonic acid is 2-ketoarabinonic acid.

11. Production process for erythritol by hydrogenation of erythrulose wherein the erythrulose is obtained by the process according to claim 10.

12. Catalytic decarboxylation process for 2-ketoaldonic acids by nickel ions according to claim 1, wherein the decarboxylation is carried out at a temperature from 70° to 90° C.

* * * * *